United States Patent [19]

Coy et al.

[11] Patent Number: 5,073,624

[45] Date of Patent: * Dec. 17, 1991

[54] THERAPEUTIC DECAPEPTIDES

[75] Inventors: David H. Coy, New Orleans, La.; Jacques-Pierre Moreau, Upton, Mass.

[73] Assignee: Administrators of the Tulane Educational Fund, New Orleans, La.

[*] Notice: The portion of the term of this patent subsequent to Sep. 12, 2006 has been disclaimed.

[21] Appl. No.: 352,140

[22] Filed: May 15, 1989

Related U.S. Application Data

[63] Continuation-in-part of Ser. No. 65,765, Jun. 23, 1987, Pat. No. 4,866,160, which is a continuation-in-part of Ser. No. 879,338, Jun. 27, 1986, abandoned, which is a continuation-in-part of Ser. No. 798,239, Nov. 14, 1985, abandoned, which is a continuation-in-part of Ser. No. 721,330, Apr. 9, 1985, abandoned.

[51] Int. Cl.$^5$ .................... C07C 103/52; A61K 37/02
[52] U.S. Cl. .................... 530/313; 530/328; 514/800
[58] Field of Search .......... 530/328, 313; 514/15, 514/885, 800; 424/451, 464

[56] References Cited

U.S. PATENT DOCUMENTS

| | | | |
|---|---|---|---|
| 4,569,967 | 2/1986 | Kornreich et al. | 525/54.11 |
| 4,642,332 | 2/1987 | Folkers et al. | 530/313 |
| 4,866,160 | 9/1989 | Coy et al. | 530/313 |

OTHER PUBLICATIONS

Folkers et al. (Abstract No. 84-30988, Naturforsch, B (39, No. 4, 528-32 (1984)).
Nestor et al. (Abstract No. 4-55672 of J. Med. Chem. 27, 1170 (1984)).
Folkers et al., (BBRC 123:1221 (1984)).

*Primary Examiner*—Nathan M. Nutter
*Attorney, Agent, or Firm*—Fish & Richardson

[57] ABSTRACT

A decapeptide of the formula: N-AC-$A^1$-$A^2$-$A^3$-Ser-$A^4$-$A^5$-$A^6$-$A^7$-$A^8$-$A^9$, wherein each $A^1$, $A^2$, and $A^3$, independently, is D-$\beta$-Nal, D-p-X-Phe (where X is halogen, H, $NH_2$, $NO_2$, OH, or $C_{1-3}$ alkyl), D-benzothienyl (2)-Ala, or D-benzothienyl (1)-Ala; $A^4$ is p-X-Phe (where X is halogen, H, $NH_2$, $NO_2$, or $C_{1-3}$ alkyl), Tyr, Lys, Arg, Leu, Trp, or Nal; $A^5$ is D-Lys, D-Tyr, D-Arg, D-Phe, D-$\beta$-Nal, D-Trp, D-homo-Arg, D-diethyl-homo-Arg, D-p-X-Phe (where X is halogen, H, $NH_2$, $NO_2$, or $C_{1-3}$ alkyl), or D-Lys-$\epsilon$-NH-R (where R is H, a branched or straight chain $C_1$-$C_{10}$ alkyl group, or an aryl group); $A_6$ is Leu, $\beta$-Nal, p-X-Phe (where X is halogen, H, $NH_2$, $NO_2$, OH, $C_2F_5$, $C_{1-3}$ alkyl), or Trp; $A^7$ is Arg, Lys, or Lys $\epsilon$-NH-R (where R is H, a branched or straight chain $C_1$-$C_6$ alkyl group, or an aryl group); $A_8$ is Pro; and $A^9$ is D-Ala, D-Ala-$NH_2$, Ala-$NH_2$, aminoisobutyric acid amide, or Gly-$NH_2$; provided that at least one of $A^2$ or $A^3$ must be D-Phe or D-Tyr, and provided further that when $A^4$ is Lys or Arg, $A^5$ must not be D-Arg, D-Lys, D-homo-Arg, D-diethyl-homo-Arg, or D-Lys-$\epsilon$-NH-R, or a pharmaceutically acceptable salt thereof.

The invention also features a method of treating T-cell-deficient patients, e.g., those suffering from Acquired Immune Dificiency Syndrome, by administering a therapeutically effective amount of an LH-RH antagonist.

17 Claims, No Drawings

THERAPEUTIC DECAPEPTIDES

This invention was made in the course of work under a grant or award from the U.S. government; therefore, the U.S. government has rights in the invention.

BACKGROUND OF THE INVENTION

This application is a continuation of U.S.S.N 065,765 filed June 23, 1987, now U.S. Pat. No. 4,866,160, which is a continuation-in-part of U.S.S.N. 879,338, filed June 27, 1986, abandoned, which is a continuation-in-part of U.S.S.N. 798,239, filed Nov. 14, 1985, now abandoned, which is a continuation-in-part of U.S.S.N. 721,330, filed Apr. 9, 1985, now abandoned.

This invention relates to therapeutic peptides

A number of luteinizing hormone releasing hormone (LH-RH) analogs have been described which inhibit the release of LH-RH, a peptide hormone having the formula pGlu-His-Trp-Ser-Tyr-Gly-Leu-Arg-Pro-Gly-$NH_2$. These analogs are called LH-RH antagonists. For example, Coy et al. U.S. Pat. No. 4,431,635, hereby incorporated by reference, describes LH-RH analogs having the general formula X-$R^1$-$R^2$-$R^3$-Ser-Tyr-$R^4$-Leu-Arg-Pro-$R^5$-$NH_2$, in which X can be Ac; $R^1$ and $R^4$, independently, can be D-Trp or D-p-X-Phe, where X is a halogen or methyl group; $R^2$ can be D-p-X-Phe; $R^3$ can be D-Trp; and $R^5$ can be Gly or D-Ala.

SUMMARY OF THE INVENTION

In general, the invention features a decapeptide of the formula: N-Ac-$A^1$-$A^2$-$A^3$-Ser-$A^4$-$A^5$-$A^6$-$A^7$-$A^8$-$A^9$, wherein each $A^1$, $A^2$, and $A^3$, independently, is D-$\beta$-Nal, D-p-X-Phe (where X is halogen, H, $NH_2$, $NO_2$, OH, or $C_{1-3}$ alkyl), D-benzothienyl (2)-Ala, or D benzothienyl (1) Ala; $A^4$ is p X-Phe (where X is halogen, H, $NH_2$, $NO_2$, or $C_{1-3}$ alkyl), Tyr, Lys, Arg, Leu, Trp, or Nal; $A^5$ is D-Lys, D-Tyr, D-Arg, D-Phe, D-$\beta$-Nal, D-Trp, D-homo-Arg, D-diethyl-homo-Arg, D-p X-Phe (where X is halogen, H, $NH_2$, $NO_2$, or $C_{1-3}$ alkyl) or D-Lys-$\epsilon$-NH-R (where R is H, a branched or straight chain lower ($C_1$-$C_{10}$) alkyl group, e.g., methyl, isopropyl, heptyl or butyl, or an aryl group, e.g., benzyl, p-Cl-benzyl, or $CH_2$ naphthyl); $A_6$ is Leu, $\beta$-Nal, p-X-Phe (where X is halogen, H, $NH_2$, $NO_2$, OH, $C_2F_5$ or $C_{1-3}$ alkyl), or Trp; $A^7$ is Arg, Lys, or Lys-$\epsilon$-NH-R (where R is H, a branched or straight chain lower ($C_{1-6}$) alkyl group, e.g., methyl, isopropyl, heptyl or butyl, or an aryl group, e.g., benzyl, p-Cl-benzyl, or $CH_2$ naphthyl); $A^8$ is Pro; and $A^9$ is D Ala, D-Ala-$NH_2$, Ala-$NH_2$, aminoisobutyric acid amide, or Gly-$NH_2$; provided that at least one of $A^2$ or $A^3$ must be D-Phe or D-Tyr, and provided further that when $A^4$ is Lys or Arg, $A^5$ must not be D-Arg, D-Lys, D-homo-Arg, D-diethyl-homo-Arg, or D-Lys-$\epsilon$NH-R, or a pharmaceutically acceptable salt thereof. ($\beta$-Nal refers to $\beta$-napthhylalanine; where no L- or D- designation is given herein, the L-isomer is intended.)

In one preferred decapeptide, $A^1$ is D-$\beta$-Nal, $A^2$ is D-p-Cl-Phe, $A^3$ is D-Phe, $A^4$ is Tyr, $A^5$ is D-Arg, $A^6$ is Phe, $A^7$ is Arg, $A^8$ is Pro, and $A^9$ is D-Ala.

In another preferred decapeptide, $A^1$ is D-$\beta$-Nal, $A^2$ is D-Phe, $A^3$ is D-Phe, $A^4$ is Tyr, $A^5$ is D-Arg, $A^6$ is Phe, $A^7$ is Arg, $A^8$ is Pro, and $A^9$ is D-Ala.

In another preferred decapeptide, $A^1$ is D-$\beta$-Nal, $A^2$ is D-Phe, $A^3$ is D-Phe, $A^4$ is Tyr, $A^5$ is D-Lys (isopropyl), $A^6$ is Phe, $A^7$ is Lys (isopropyl), A8 is Pro, and is Ala $NH_2$.

In another preferred decapeptide, $A^1$ is D-$\beta$-Nal, $A^2$ is D-p-Cl-Phe, $A^3$ is D-Tyr, $A^4$ is Phe, $A^5$ is D-Arg, $A^6$ is Leu, $A^7$ is Arg, $A^8$ is Pro, and $A^9$ is D-Ala.

In another preferred decapeptide, $A^1$ is D-$\beta$-Nal, $A^2$ is D-Phe, $A^3$ is D-Phe, $A^4$ is Phe, $A^5$ is D-Arg, $A^6$ is Leu, $A^7$ is Arg, $A^8$ is Pro, and $A^9$ is D-Ala.

In another preferred decapeptide, $A^1$ is D-$\beta$-Nal, $A^2$ is D-Phe, $A^3$ is D Phe, $A^4$ is Tyr, $A^5$ is D-Lys (isopropyl), $A^6$ is Phe, $A^7$ is Arg, $A^8$ is Pro, and $A^9$ is D-Ala-$NH_2$.

In other preferred embodiments, a therapeutically effective amount of the therapeutic decapeptide and a pharmaceutically acceptable carrier substance, e.g., magnesium carbonate or lactose, together form a therapeutic composition for inhibiting the release of sex hormones, particularly LH, induced by LH-RH. This composition can be in the form of a pill, tablet, capsule, liquid, or sustained release tablet for oral administration; a liquid spray for nasal administration; or a liquid for intravenous, subcutaneous, parenteral, or intraperitoneal administration.

Another preferred form for administration is an injectible suspension of the peptide with a bioerodible, biocompatible polymer matrix capable of effecting sustained release of the peptide. Other suitable forms are peptide/polymer implants, transdermal patches, transmucosal patches and compositions usable with iontophoretic techniques.

The decapeptides of the invention are active in inhibiting the LH-RH induced release of LH, and exhibit a long duration of activity, thus minimizing the amount and frequency of dosages. Furthermore, manufacture is relatively simple and inexpensive. In addition, the peptides have the advantage of being able to be administered orally, a property owing to their high lipophilicity and their ability to withstand degradation.

The peptides of the invention have D-Phe or D-Tyr at at least one of positions $A^2$ or $A^3$ D-Phe or D-Tyr at position $A^3$ have been found to be modifications of particular importance in terms of activity, while D-Phe at position $A^2$ provides further cost reduction, compared to D-p-X-Phe at $A^2$, without significant comparative loss of activity. D-Phe at $A^2$ and D-Tyr at $A^3$ also lessen the irritant effect of the decapeptide, as does the presence of D-Lys-$\epsilon$-NH-R at position $A^5$ and Lys e NH-R at position $A^7$ when R is an alkyl or aryl group. Presumably, this is due to an observed decrease in histamine releasing activity. It is further believed that the presence of Arg at position $A^4$ and D-Tyr at position $A^5$, known as the Hodgen modification, also decreases histamine-releasing activity. p-X-Phe at position $A^6$ is also particularly advantageous in terms of activity.

It has also been discovered that LH-RH antagonists in general, and the above-described decapeptides in particular, can be used to treat patients suffering from Acquired Immune Deficiency Syndrome (AIDS) when administered as described above. The antagonists rejuvenate the thymus, which then produces T-cells to replace T-cells destroyed by the AIDS virus.

The peptides of the invention can be used to treat some forms of hormone dependent cancers including breast and prostate. It has also been discovered that the LHRH antagonists of the invention can exhibit a direct antitumoral effect in human mammary cancer cell lines (e.g. MCF-7).

Other features and advantages of the invention will be apparent from the following description of the preferred embodiments thereof, and from the claims.

DESCRIPTION OF THE PREFERRED EMBODIMENTS

We now describe the structure, synthesis, and use of preferred embodiments of the invention.

Structure

The decapeptides of the invention have the general formula recited in the Summary of the Invention above. They all have an acetyl group at the amino terminal end in addition to Ser at position 4. Substitution of non natural substituents at positions other than $A^2$, $A^3$, and $A^6$ can be used to modify the properties of the compound, and will not prevent the $A^2$, $A^3$, and/or $A^6$ substituents from providing their beneficial effects.

The decapeptides can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, trifluoroacetic, or pamoic acid, as well as polymeric acids such as tannic acid or carboxymethyl cellulose, and salts with inorganic acids such as the hydrohalic acids, e.g., hydrochloric acid, sulfuric acid, or phosphoric acid.

Synthesis

EXAMPLE 1

The synthesis of N-Ac-D-$\beta$-Nal-D-Phe-D-Phe-Ser-Tyr-D-Arg-Phe-Arg-Pro-D-Ala follows.

Other decapeptides of the invention can be prepared by making appropriate modifications of the following synthetic method.

The first step is the preparation of N-Acetyl-D-$\beta$-Nal-D-Phe-D-Phe-benzyl-Ser-Tyr-D-tosyl-Arg-Phe-tosyl-Arg-Pro-D-Ala-benzyhdrylamine-resin, as follows.

Benzyhydrylamine polystyrene resin (Bachem, Inc.) (1.00 g, 0.3 mmole) in the chloride ion form is placed in the reaction vessel of a Beckman 990B peptide synthesizer programmed to perform the following reaction cycle: (a) $CH_2Cl_2$; (b) 33% trifluoroacetic acid in $CH_2Cl_2$ (2 times for 1 and 25 min each); (c) $CH_2Cl_2$; (d) ethanol; (e) $CH_2Cl_2$; (f) triethylamine in $CHCl_3$; and (g) $CH_2Cl_2$.

The neutralized resin is stirred with alpha-t-butoxycarbonyl (Boc)-D-Ala and diisopropylcarbodiimide (1.5 mmole) in $CH_2Cl_2$ for 1 hour and the resulting amino acid resin is then cycled through steps (a) to (g) in the above wash program. The following amino acids (1.5 mmole) are then coupled successively by the same procedure: Boc-Pro, Boc-Tosyl-Arg, Boc-Phe, Boc-Tosyl-D-Arg, Boc-Tyr, Boc-benzyl-S-er, Boc-D-Phe, and Boc-D-$\beta$-Nal.

After removal of the N terminal Boc group, the peptide benzyhydrylamine resin is neutralized and acetylated by treatment with 5% acetic acid in $CH_2Cl_2$. The completed resin is then washed with $CH_3OH$ and air dried.

From the above resin is prepared N-Ac-D-$\beta$-Nal-D-Phe-D-Phe-Ser-Tyr-D-Arg-Phe-Arg-Pro-D-Ala, as follows.

A mixture of the above decapeptide resin (1.85 g, 0.5 mmole) and a solution of 4 ml anisole, 100 mg dithiothreitol, and 36 ml hydrogen fluoride is stirred at 0° C. for 45 minutes. Excess hydrogen fluoride is evaporated rapidly under a stream of dry nitrogen, after which the free peptide is precipitated and washed with ether.

The peptide is then dissolved in a minimum volume of 50% acetic acid and eluted on a column (2.5×100 mm) of Sephadex G 25. Fractions containing a major component, as determined by u.v. absorption and thin layer chromatography (tlc), are pooled and evaporated to a small volume in vacuo. This solution is applied to a column (2.5×50 cm) of octadecylsilane silica (Whatman LRP 1, 15-20 um mesh size) which is eluted with a linear gradient of 15-50% acetonitrile in 20% acetic acid in water. Fractions are examined by tlc and analytical high performance liquid chromatography (hplc) and pooled to give maximum purity. Repeated lyophilization of the solution from water gives 117 mg of the product as a white, fluffy powder.

This material is found to be homogeneous by hplc and tlc. Amino acid analysis of an acid hydrolysate confirms the composition of the decapeptide.

N-Ac-D-$\beta$-Nal-D-p-Cl-Phe-D-Tyr-Ser-Phe-D-Arg-Leu-Arg-Pro-D-Ala was prepared according to the synthesis described above, substituting Boc-D-p-Cl-Phe for Boc-D-Phe at position $A^2$, Boc-D-Trp for Boc-D-Phe at position $A^3$, Boc-Phe for Boc-Tyr at position $A^4$, and Boc-Leu for Boc Phe at $A^6$.

N-Ac-D-$\beta$Nal-D-p-Cl-Phe-D-Tyr-Ser-Phe-D-Arg-Leu-A rg-Pro-D-Ala was prepared according to the synthesis described above, substituting Boc-D-p-Cl-Phe for Boc-D-Phe at position $A^2$, Boc-D-Tyr for Boc-D-Phe at position $A^3$, Boc-Phe for Boc-Tyr at position $A^4$, and Boc-Leu for Boc-Phe at position $A^6$.

N-Ac-D-$\beta$-Nal-D-Phe-D-Phe-Ser-Phe-D-Arg-Leu-Arg-Pr o-D-Ala was prepared according to the synthesis described above, substituting Boc-Phe for Boc-Tyr at $A^4$ and Boc-Leu for Boc Phe at $A^6$.

EXAMPLE 2

To synthesize peptides featuring D-Lys-$\epsilon$-NH-R at position $A^5$ or Lys-$\epsilon$-NH-R at position 7, where R is an alkyl or aryl group, there is used the method described in Coy, et al., U.S. Pat. application Ser. No. 879,348, filed June 27, 1986 and assigned to the same assignee as this application, hereby incorporated by reference. In general, the synthesis involves reacting a carbonyl-containing compound, e.g., acetone or formaldehyde, with a resin bound polypeptide featuring a Lys or D-Lys subunit in the presence of sodium cyanoborohydride. The carbonyl containing compound reacts with the free $\epsilon$-$NH_2$ group on the side chain of the Lys or D-Lys subunit; reaction with acetone produces an $\epsilon$-N isopropyl moiety, whereas reaction with formaldehyde produces an $\epsilon$-N methyl moiety.

The synthesis of Ac-D-$\beta$-Nal-D-Phe-D-Phe-Ser-Tyr-D-Lys (isopropyl) Phe-Lys (isopropyl)-Pro-Ala-$NH_2$ follows.

Ac-D-$\beta$-Nal-D-Phe-D-Phe-Ser (Bzl)-Tyr-D-Lys (FMOC)-Phe-D-Lys (FMOC)-Pro-D-Ala-benzhydrylamine resin (BzL=benzyl; FMOC=fluorenylmethyloxycarbonyl) was prepared by standard methods in a Beckman 990B automatic peptide synthesizer using 33% TFA (trifluoroacetic acid) for removal of the $\alpha$-BOC protecting groups. The $\epsilon$-FMOC protecting groups on the Lys residues are completely stable to these acidic conditions, and to subsequent neutralization steps with 10% triethylamine in chloroform. The resin was then treated with 50ml of a 50% solution of piperidine in DMF (dimethylformamide) for about 12h to remove the FMOC protecting groups from the Lys residues.

To react the free ε-amino groups of the Lys residues, the resin (0.25 mmole) was mixed with 5ml of acetone, and 1 mmole of sodium cyanoborohydride in DMF/1% acetic acid added. The resin mixture was then stirred until it was negative to ninhydrin reaction (about 3h); the negative ninhydrin reaction indicated that the free ε-amino groups had been converted to N-isopropyl amino groups.

The resin was then cleaved from the support by treatment with HF/anisole and purified under standard conditions to yield the desired polypeptide.

Ac-D-Nal-D-Phe-D-Phe-Ser-Tyr-D-Lys (isopropyl)-Phe-Arg-Pro-D-Ala amide is prepared in analogous fashion using appropriate modifications of the above-described procedure.

Use

When administered to a mammal (e.g., orally, intravenously, parenterally, nasally, or by suppository), the decapeptides are effective in inhibiting the release of LH induced by LH-RH.

The decapeptides of the invention can be used for the treatment of precocious puberty, hormone dependent tumors (e.g., malignant and benign prostatic, mammary, ovarian and testicular tumors), hirsutism, acne, amenorrhea (e.g., secondary amenorrhea), endometriosis, and ovarian and mammary cystic diseases; the particular decapeptide described above is particularly effective in preventing the growth of mammary tumors. The decapeptides can also be used to regulate human menopausal gonadotropin luteinizing hormone (LH) and follicle-stimulating hormone (FSH) during perimenopausal and postmenopausal periods in women. The decapeptides can also be used as female contraceptives and as an abortifacient. The decapeptides can also be useful in the symptomatic relief of the premenstrual syndrome.

The decapeptides can be administered to a patient in a dosage of 10 mcg/kg/day to 1000 mcg/kg/day, preferably 25–250 mcg/kg/day.

The decapeptides, and LH-RH antagonists in general, can also be used to treat patients suffering from AIDS. Examples of additional LH RH antagonists are described in Coy, U.S. Pat. No. 4,647,653, hereby incorporated by reference, and Coy et al., U.S. Pat. No. 4,431,635, previously incorporated by reference. The LH-RH antagonists rejuvenate the thymus when administered as described above. The thymus then produces T-cells to replace the T-cells destroyed by the AIDS virus, thereby compensating for the effects of the virus.

Other embodiments are within the following claims.

We claim:

1. A decapeptide of the formula: N-Ac-$A^1$-$A^2$-$A^3$-Ser-$A^4$-$A^5$- $A^6$-$A^7$-$A^8$-$A^9$, wherein each $A^1$, $A^2$, and $A^3$, independently, is D-β-Nal, D p-X Phe (where X is halogen, H, $NH_2$, $NO_2$, OH, or $C_{1-3}$ alkyl), D benzothienyl (2) Ala, or D-benzothienyl (1)-Ala; $A^4$ is p X Phe (where X is halogen, H, $NH_2$, $NO_2$, or $C_{1-3}$ alkyl), Tyr, Lys, Arg, Leu, Trp, or Nal; $A^5$ is D Lys, D Tyr, D Arg, D-Phe, β-Nal, D-β-Nal, D-Trp, D-homo-Arg, D-diethyl-homo Arg, D-p-X-Phe (where X is halogen, H, $NH_2$, $NO_2$, or $Cl_{1-3}$ alkyl) or D-Lys-ε-NH-R (where R is H, a branched or straight chain $C_1C_{10}$ alkyl group, or an aryl group); $A_6$ is Leu, β-Nal, p-X-Phe (where X is halogen, H, $NH_2NO_2$, OH, $C_2F_5$, or $C_{1-3}$ alkyl), or Trp; $A^7$ is Arg, Lys, or Lys-ε-NH-R (where R is H, a branched or straight chain $C_1$-$C_{10}$ alkyl group, or an aryl group); $A_8$ is Pro; and $A^9$ is D-Ala, D-Ala-$NH_2$, Ala-$NH_2$, aminoisobutyric acid amide, or Gly $NH_2$, provided that at least one of $A^2$ or $A^3$ must be D-Phe or D-Tyr, and provided further that when $A^4$ is Lys or Arg, $A^5$ must not be D-Lys, D-Arg, D-homo-Arg, D-diethyl-homo-Arg, or D-Lys-ε-NH-R, or a pharmaceutically acceptable salt thereof.

2. The decapeptide of claim 1 wherein $A^3$ is D-Phe.

3. The decapeptide of claim 1 or claim 2 wherein $A^2$ is D-Phe.

4. The decapeptide of claim 1 or claim 2 wherein $A^6$ is p-X-Phe.

5. The decapeptide of claim 1 wherein $A^1$ is D-β-Nal, $A^2$ is D-p-Cl-Phe, $A^3$ is D-Phe, $A^4$ is Tyr, $A^5$ is D-Arg, $A^6$ is Phe, $A^7$ is Arg, $A^8$ is Pro, and $A^9$ is D-Ala.

6. The decapeptide of claim 1 wherein $A^1$ is D-β-Nal, $A^2$ is D-Phe, $A^3$ is D-Phe, $A^4$ is Tyr, $A^5$ is D-Arg, $A^6$ is Phe, $A^7$ is Arg, $A^8$ is Pro, and $A^9$ is D-Ala.

7. The decapeptide of claim 1 wherein $A^1$ is D-β-Nal, $A^2$ is D-Phe, $A^3$ is D-Phe, $A^4$ is Tyr, $A^5$ is D-Lys (isopropyl), $A^6$ is Phe, $A^7$ is Lys (isopropyl), $A^8$ is Pro, and $A^9$ is Ala-$NH_2$.

8. The decapeptide of claim 1 wherein $A^1$ is D-β-Nal, $A^2$ is D-Phe, $A^3$ is D-Phe, $A^4$ is Phe, $A^5$ is D-Arg, $A^6$ is Leu, $A^7$ is Arg, $A^8$ is Pro, and $A^9$ is D-Ala.

9. The decapeptide of claim 1 wherein $A^1$ is D-β-Nal, $A^2$ is D-Phe, $A^3$ is D-Phe, $A^4$ is Tyr, $A^5$ is D-Lys (isopropyl), $A^6$ is Phe, $A^7$ is Arg, $A^8$ is Pro, and $A^9$ is D-Ala-$NH_2$.

10. The decapeptide of claim 1 wherein $A^1$ is D-β-Nal, $A_2$ is D-p-Cl-Phe, $A^3$ is D-Tyr, $A^4$ is Phe, $A^5$ is D-Arg, $A^6$ is Leu, $A^7$ is Arg, $A^8$ is Pro, and $A^9$ is D-Ala.

11. A therapeutic composition for inhibiting the LH-RH induced release of sex hormones comprising a therapeutically effective amount of the decapeptide of claim 1 together with a pharmaceutically acceptable carrier substance.

12. A method of treating a mammal in need of inhibition of LH RH induced release of sex hormones comprising administering to said mammal a therapeutically effective amount of the decapeptide of claim 1.

13. The composition of claim 11 wherein said composition is in the form of a pill, tablet, capsule, liquid, or sustained release tablet for oral administration to a patient in need of said decapeptide.

14. The composition of claim 11 wherein said composition is in the form of a liquid capable of being administered intravenously, subcutaneously, parenterally, or intraperitoneally to a patient in need of said decapeptide.

15. The composition of claim 11 wherein said composition is in the form of an injectible suspension comprising said decaptide and a bioerodible, biocompatible polymer matrix capable of effecting sustained release of said decapeptide.

16. The composition of claim 11 wherein said composition is in the form of a decapeptide/bioerodible, biocompatible implant.

17. The composition of claim 11 wherein said composition is a transdermal patch or transmucosal patch.

* * * * *